(12) United States Patent
Chi et al.

(10) Patent No.: US 10,815,175 B1
(45) Date of Patent: Oct. 27, 2020

(54) METHOD OF FABRICATING DIOL CONTAINING BIS-CYCLOALIPHATE

(71) Applicant: CPC Corporation, Taipei (TW)

(72) Inventors: Ching-Fa Chi, Chiayi (TW); Ying-Chieh Yang, Chiayi (TW); Yi-Hui Chen, Chiayi (TW); Chyi-Liuh Ho, Chiayi (TW); Yih-ping Wang, Chiayi (TW)

(73) Assignee: CPC Corporation, Taiwan, Taipei (TW)

( * ) Notice: Subject to any disclaimer, the term of this patent is extended or adjusted under 35 U.S.C. 154(b) by 0 days.

(21) Appl. No.: 16/807,211

(22) Filed: Mar. 3, 2020

(51) Int. Cl.
 *C07C 29/20* (2006.01)
(52) U.S. Cl.
 CPC ................................. *C07C 29/20* (2013.01)
(58) Field of Classification Search
 CPC . C07C 29/20; C07C 2521/06; C07C 2523/42; C07C 2523/44; C07C 2543/46
 See application file for complete search history.

(56) References Cited

U.S. PATENT DOCUMENTS

| 5,942,645 A | * | 8/1999 | Rutter | B01J 23/462 |
| | | | | 502/330 |
| 9,084,983 B2 | * | 7/2015 | Konigsmann | B01J 37/0205 |

FOREIGN PATENT DOCUMENTS

DE 102015219729 A1 * 4/2016 ............. B01J 23/46

OTHER PUBLICATIONS

Yen et al. Hydrogenation of bisphenol A—Using a mesoporous silica based nano ruthenium catalyst Ru/MCM-41 and water as solvent. Catalysis Today, vol. 174, 121-126. (Year: 2011).*

* cited by examiner

*Primary Examiner* — Sikarl A Witherspoon
(74) *Attorney, Agent, or Firm* — Demian K. Jackson; Jackson IPG PLLC

(57) ABSTRACT

A method is provided for fabricating a diol containing a bis-cycloaliphate. The diol is hydrogenated with hydrogen and a catalyst. Therein, the diol has a bis-aromatic. The catalyst comprises an active metal and a catalyst carrier. The active metal is a VIII-B-group transition element. The catalyst carrier is an oxide of IV-B-group element. Thus, the diol containing the bis-cycloaliphate is generated.

6 Claims, 6 Drawing Sheets

| Reactant | Reaction pressure (Bar) | Reaction temperature (°C) | Reactant flow (ml/min) | H₂ flow (L/hr) | Conversion (%) | Selectivity (%) |
|---|---|---|---|---|---|---|
| BPA | 20 | 80 | 0.041 | 1.1 | 99.99 | 98.77 |
| | | | 0.062 | 1.7 | 99.99 | 98.63 |
| | | | 0.083 | 2.2 | 99.98 | 98.76 |

FIG.1

| Reactant | Reaction pressure (Bar) | Reaction temperature (°C) | Reactant flow (ml/min) | H₂ flow (L/hr) | Conversion (%) | Selectivity (%) |
|---|---|---|---|---|---|---|
| BPA | 10 | 70 | 0.041 | 1.1 | 99.95 | 98.93 |
| | 20 | | 0.041 | 1.1 | 99.95 | 98.86 |
| | 30 | | 0.041 | 1.1 | 99.96 | 98.96 |

FIG.2

| Reactant | Reaction pressure (Bar) | Reaction temperature (°C) | Reactant flow (ml/min) | H₂ flow (L/hr) | Conversion (%) | Selectivity (%) |
|---|---|---|---|---|---|---|
| BPA | 40 | 80 | 0.041 | 1.1 | 100 | 98.79 |
| | | 90 | 0.041 | 1.1 | 100 | 98.2 |

FIG.3

| Reactant | Reaction pressure (Bar) | Reaction temperature (°C) | Reactant flow (ml/min) | H₂ flow (L/hr) | Conversion (%) | Selectivity (%) |
|---|---|---|---|---|---|---|
| BPA | 40 | 80 | 0.062 | 1.7 | 100 | 98.79 |
| | | | 0.083 | 2.2 | 100 | 98.59 |

FIG.4

| Reactant | Reaction pressure (Bar) | Reaction temperature (°C) | Reactant flow (ml/min) | $H_2$ flow (L/hr) | Conversion (%) | Selectivity (%) |
|---|---|---|---|---|---|---|
| BPAEO | 10 | 60 | 0.060 | 0.87 | 100 | 99.0 |
|  | 10 | 60 | 0.117 | 1.75 | 99.9 | 99.2 |
|  | 5 | 70 | 0.082 | 2.46 | 99.8 | 98.2 |
|  | 10 | 70 | 0.120 | 3.50 | 99.9 | 98.0 |

FIG.5

| Reactant | Reaction pressure (Bar) | Reaction temperature (°C) | Reactant flow (ml/min) | H₂ flow (L/hr) | Conversion (%) | Selectivity (%) |
|---|---|---|---|---|---|---|
| BPAEO4 | 10 | 70 | 0.06 | 1.75 | 99.9 | 99.99 |
| | 20 | 60 | 0.06 | 1.75 | 100 | 99.99 |

FIG.6

METHOD OF FABRICATING DIOL CONTAINING BIS-CYCLOALIPHATE

TECHNICAL FIELD OF THE INVENTION

The present invention relates to fabricating a diol; more particularly, to hydrogenating an aromatic, where a corresponding diol containing a bis-cycloaliphate is generated through hydrogenation with a diol solution containing a bis-aromatic.

DESCRIPTION OF THE RELATED ARTS

Hydrogenated bisphenol A (HBPA) is obtained through hydrogenation with bisphenol A (BPA). Corresponding alicyclic-ring compounds are generated by saturating benzene rings for producing epoxy resins and unsaturated polyester resins. The synthetized materials has good weathering resistance, corona resistance, tracking resistance, high dielectric strength, chemical resistance, and so on. Diol derivatives are formed by reaction of bisphenol A with ethylene glycol can be applied in many fields, like polyester, paints, and PU. However, each of the structures of these compounds contains two benzene rings, which will affect the characteristics of the products and result in limited applications. The cycloaliphatic structures are obtained through hydrogenating benzene ring will significantly increase its value in applications.

Current commercial processes of hydrogenated bisphenol A mostly use batch reactors. In the mean time, they are operated in environments of high pressure (greater than 100 bar), high temperature (greater than 100 degrees Celsius(° C.)), or both high pressure and high temperature, which result in high cost of investment, subsequent operation and maintenance. The bottlenecks they face include low catalyst selectivity and poor catalyst stability. Therefore, how to enhance catalytic activity and lower reaction temperature or pressure with product purity and yield taken into account for reducing investment cost, lowering subsequent purification cost, and improving overall economic efficiency becomes crucial.

Hence, the prior arts do not fulfill all users' requests on actual use.

SUMMARY OF THE INVENTION

The main purpose of the present invention is to hydrogenate a diol containing a bis-aromatic, where a corresponding diol containing a bis-cycloaliphate is fabricated at a low temperatures under a low pressure; the temperature for reaction is only 50~100° C., the pressure is 1~50 bar, the conversion reaches more than 99.8%, and the product selectivity reaches more than 98%; and, thus, by-product formation is limited and the cost of separation and purification that follows is reduced to improve overall economic efficiency.

To achieve the above purpose, the present invention is a method of fabricating a diol containing a bis-cycloaliphate, where, in a reactor with the presence of a catalyst under an environment of hydrogen, a diol solution containing a bis-aromatic is obtained to generate a corresponding diol containing a bis-cycloaliphate; the catalyst comprises an active metal, which is a first element of VIII-B-group transition element in the periodic table, including nickel, platinum, palladium, ruthenium, or rhodium; or is a combination of some of the above elements, and a catalyst carrier, which is an oxide of a second element of IV-B-group in the periodic table, including Ti, Zr, and Ha; the diol solution comprises a diol and a solvent; the diol contains the bis-aromatic; the diol is bisphenol A or ethoxylated bisphenol A (BPAEO); the solvent is a monohydric alcohol, which is methanol, ethanol, propanol, isopropanol, isobutanol, cyclohexanol, or nonanol, or a combination of monohydric alcohols; and the BPAEO has a structure as follows:

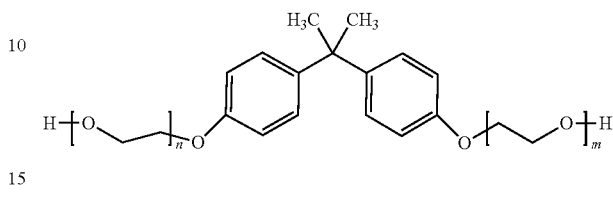

and m+n=2~4.

BRIEF DESCRIPTION OF THE DRAWINGS

The present invention will be better understood from the following detailed description of the preferred embodiment according to the present invention, taken in conjunction with the accompanying drawings, in which FIG. 1 to FIG. 6 are the views showing results and conditions of hydrogenation with the diol containing the bis-aromatic.

DESCRIPTION OF THE PREFERRED EMBODIMENT

The following description of the preferred embodiment is provided to understand the features and the structures of the present invention.

Please refer to FIG. 1 to FIG. 6, which are views showing results and conditions of hydrogenation with the diol containing the bis-aromatic. As shown in the figures, the present invention is a method of fabricating a diol containing a bis-cycloaliphate, where the method processes hydrogenation with a diol containing a bis-aromatic in the presence of hydrogen and a catalyst. The diol is a bisphenol A (BPA) or an ethoxylated bisphenol A (BPAEO), where the BPAEO has a structure as follows:

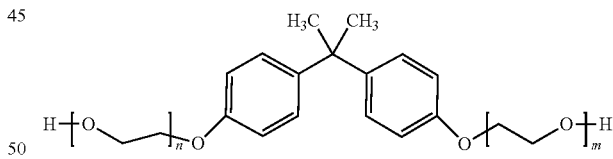

and m+n=2~4. Basically, the BPAEO uses the catalyst to obtain a product of a diol containing a bis-cycloaliphate through hydrogenation in the presence of hydrogen, where the product has a structure as follows:

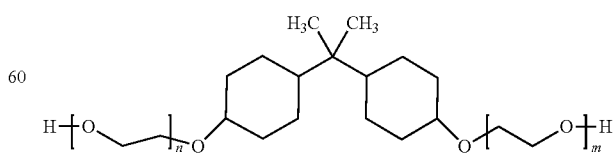

and m+n=2~4.

At first, a catalyst is placed in a reactor. Then, a diol solution containing a bis-aromatic is pumped into the reactor accompanying with hydrogen fed in for hydrogenation. The reactor is a continuous reactor like a trickle-bed reactor, a stir-tank reactor, a bubble-column reactor, or a multi-tube reactor; or a non-continuous reactor like a batchwise reactor. The reactor has a reaction pressure of 1~60 bar while a preferred reaction pressure is 1~40 bar and a best reaction pressure is 1~20 bar, and a reaction temperature of 40~120 degrees Celsius (° C.) while a preferred reaction temperature is 40~100° C. and a best reaction temperature is 40~80° C.

The present invention processes the reaction under the condition of the existence of the catalyst. The catalyst is contained in the reactor. The catalyst comprises a catalyst carrier and an active metal. Therein, the catalyst carrier is an oxide of an element of IV-B group in the periodic table; the oxide of the element of IV-B group is an oxide of a metal or a combination of metals and the metal is titanium (Ti), zirconium (Zr), or hafnium (Ha); the active metal is a transition metal of VIII-B-group element in the periodic table, which is nickel (Ni), platinum (Pt), palladium (Pd), ruthenium (Ru), or rhodium (Rh); or is a combination of some of the above elements; and the active metal occupies 0.5~12 weight percent (wt %) of said catalyst while 0.5~10 wt % is preferred and 0.5~8 wt % is the best.

The catalyst carrier is obtained by dissolving a IV-B-group metal salt into a solvent, and, then, an alkaline solution is gradually added in to adjust the pH value of the mixed solution to 8~12. The IV-B-group metal salt is zirconium oxychloride ($ZrOCl_2$), zirconium oxynitrate ($ZrO(NO_3)_2$), zirconyl hydroxynitrate ($ZrO(OH)NO_3$), zirconium oxysulfate ($ZrOSO_4$), titanium oxychloride ($TiOCl_2$), or titanium oxynitrate ($TiO(NO_3)_2$), or is a mixture of some of the above compounds. The alkaline solution is a solution of sodium hydroxide, potassium hydroxide, sodium carbonate, or ammonia solution; or a mixed solution of some of the above compounds.

Then, the above solution is stayed still for 1~24 hours (hrs) under a room temperature of 25~110° C. Then, the above solution is processed through filtration, water washing, and drying to form the catalyst carrier. In a state-of-use, a drying temperature is 100~150° C., and a drying time is 12~24 hrs.

Then, a metal of Ruthenium is processed to be loaded on the catalyst carrier by using a precursor containing the metal of Ru like ruthenium chloride hydrate ($RuCl_3 \cdot nH_2O$), ruthenium trinitro-nitrite ($Ru(NO_3)_3 \cdot NO$), or ruthenium oxide ($RuO_2$). In a state-of-use, The precursor containing the metal of Ru is impregnated into the catalytic carrier through deposition precipitation or incipient wetness impregnation, where the impregnation is processed at a room temperature of 25~60° C. for a time of 1~5 hrs, and the concentration range of Ru is 1~5 wt %.

Then, drying and calcination are processed. In a state-of-use, a drying temperature is 100~150° C., a drying time is 12~24 hrs; a calcination temperature is 300~550° C., and a calcination time is 4~18 hrs.

Then, a hydrogenation reaction is followed as described below.

The prepared catalyst is put into the reactor. The catalyst comprises the catalyst carrier of the oxide of the element of IV-B group and the active metal of the VIII-B group transition element contenting 1~5 wt %. The reactor is a continuous reactor like a trickle-bed reactor, a stir-tank reactor, a bubble-column reactor, or a multi-tube reactor; or a non-continuous reactor like a batchwise reactor.

Then, a diol solution containing a bis-aromatic is put in the reactor and hydrogen is simultaneously fed into the reactor. The diol solution containing the bis-aromatic comprises a reactant (a diol containing the bis-aromatic) and a solvent. The reaction is processed in the presence of the solvent or a diluent, The choice of solvent or diluent needs to consider compatibility with the principal reactant to avoid phase separation or immiscibility, and not to involve in the reaction during hydrogenation; and, furthermore, the product itself obtained after the hydrogenation can also be used as the solvent or diluent. In a state-of-use, the solvent is a monohydric alcohol or a combination of monohydric alcohols, and the monohydric alcohol is methanol, ethanol, propanol, isopropanol, isobutanol, cyclohexanol, or nonanol. In a state-of-use, the diol solution containing the bis-aromatic has a concentration of 5~30 wt %.

In a state-of-use, the reactor containing the catalyst, hydrogen, and the diol solution containing the bis-aromatic is heated up for hydrogenation to form a corresponding diol containing a bis-cycloaliphate. In a state-of-use, the temperature of the reaction is 50~100° C. In another state-of-use, the temperature of the reaction is 50~70° C. and the pressure of the reaction is 5~50 bar. In another state-of-use, the pressure of the reaction is 5~20 bar. The time of the reaction is appropriately adjusted according to the type of the reactor and the quality of the product. For a continuous reactor like a trickle-bed reactor or a multi-tube reactor, a space velocity must be set; and, for a stirred-tank reactor or a non-continuous batchwise reactor, the time of the reaction must be appropriately adjusted according to the quality of the product. After removing the solvent of the product obtained after hydrogenation, a desired hydrogenated product is obtained and the solvent is recycled.

[Fabrication] Catalyst A 24.6 grams (g) of nitrate of zirconium oxide is dissolved in 200 milli-liters (mL) of deionized water; and, then, sodium carbonate or ammonia (or a mixture of both) is added for coprecipitation to be followed with a stay of 4~24 hrs. Then, the solution obtained after being stayed is filtered, washed, and dried. Then, after a process of high-temperature calcination at 600~800° C., a catalyst carrier is obtained.

10 g of 20~30-meshed particles of the catalyst carrier is obtained after crushing and sieving. Through incipient wetness impregnation, an appropriate amount of a solution of ruthenium chloride or ruthenium(III) nitrosyl nitrate is impregnated onto the catalyst carrier. Then, after a process of high-temperature calcination at 400° C., a catalyst (Catalyst A) containing 3 wt % of ruthenium is obtained.

The present invention discloses a hydrogenation reaction with a catalyst comprising a catalyst carrier and an active metal along with a diol containing a bis-aromatic to be processed by using the diol containing the bis-aromatic as a reactant to obtain the following results under the following conditions:

[State-of-Use 1]

2 mL of 20~30-meshed Catalyst A is filled in the reactor for reduction at 250° C. in a hydrogen atmosphere, where, after cooling, isopropanol is used as a solvent to obtain a solution containing 10 wt % of BPA fed into the reactor by a feeding pump for hydrogenation. After the reaction, the products are collected for quantitative measurement. The conversion and selectivity are analyzed by gas chromatograph (GC), respectively. The operating conditions and the corresponding results are shown in FIG. 1

[State-of-Use 2]

2 mL of 20~30-meshed Catalyst A is filled in the reactor for reduction at 250° C. in a hydrogen atmosphere, where, after cooling, isopropanol is used as a solvent to obtain a solution containing 10 wt % of BPA fed into the reactor by a feeding pump for hydrogenation. After the reaction, the products are collected for quantitative measurement. The conversion and selectivity are analyzed by gas chromatograph (GC), respectively. The operating conditions and the corresponding results are shown in FIG. 2

[State-of-Use 3]

2 mL of 20~30-meshed Catalyst A is filled in the reactor for reduction at 250° C. in a hydrogen atmosphere, where, after cooling, isopropanol is used as a solvent to obtain a solution containing 15 wt % of BPA fed into the reactor by a feeding pump for hydrogenation. After the reaction, the products are collected for quantitative measurement. The conversion and selectivity are analyzed by gas chromatograph (GC), respectively. The operating conditions and the corresponding results are shown in FIG. 3.

[State-of-Use 4]

2 mL of 20~30-meshed Catalyst A is filled in the reactor for reduction at 250° C. in a hydrogen atmosphere, where, after cooling, isopropanol is used as a solvent to obtain a solution containing 15 wt % of BPA fed into the reactor by a feeding pump for hydrogenation. After the reaction, the products are collected for quantitative measurement. The conversion and selectivity are analyzed by gas chromatograph (GC), respectively. The operating conditions and the corresponding results are shown in FIG. 4

[State-of-Use 5]

7 mL of 20~30-meshed Catalyst A is filled in the reactor for reduction at 250° C. in a hydrogen atmosphere, After cooling, isopropanol is obtained as a solvent to obtain a BPAEO, which has a structure as follows (where m+n=2 has a portion of 85%; m+n=3, 12%; and m+n=4, 3%):

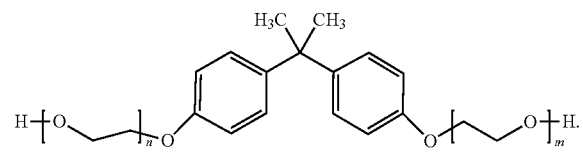

A solution containing 10 wt % of the BPAEO is fed into the reactor by a feeding pump for hydrogenation. After the reaction, the products are collected for quantitative measurement. The conversion and selectivity are analyzed by liquid chromatography-UV (LC-UV) while product selectivity is calculated with OH value. The operating conditions and the corresponding results are shown in FIG. 5:

[State-of-Use 6]

7 mL of 20~30-meshed Catalyst A is filled in the reactor for reduction at 250° C. in a hydrogen atmosphere, After cooling, isopropanol is obtained as a solvent to obtain a BPAEO4, whose structure is shown as follows (where m+n=4):

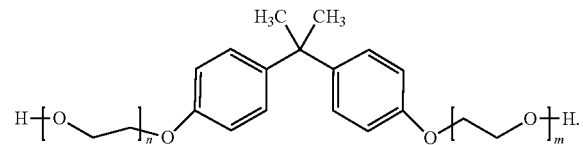

A solution containing 10 wt % of the BPAEO4 is fed into the reactor by a feeding pump for hydrogenation. After the reaction, the products are collected for quantitative measurement. The conversion and selectivity are analyzed by liquid chromatography-UV (LC-UV) while product selectivity is calculated with OH value. The operating conditions and the corresponding results are shown in FIG. 6:

Thus, the present invention provides a method hydrogenating a diol containing a bis-aromatic, where a corresponding diol containing a bis-cycloaliphate is fabricated at a low temperatures under a low pressure. In the mean time, the present invention has the following advantages: the temperature for reaction is only 50~100° C.; the pressure is 1~50 bar, the conversion reaches more than 99.8%; and, at the same time, the product selectivity reaches more than 98%, while by-product formation is limited and the cost of separation and purification that follows is reduced to further improve overall economic efficiency.

To sum up, the present invention is a method of fabricating a diol containing a bis-cycloaliphate, where a method is provided to generate a corresponding diol containing a bis-cycloaliphate through hydrogenation with a diol solution containing a bis-aromatic; the hydrogenation is processed in an environment of a low pressure (<50 bar) and a low temperature (<100° C.), the conversion reaches more than 99.8% and the product selectivity reaches more than 98%; and, thus, by-product formation is limited and the cost of separation and purification that follows is reduced to improve overall economic efficiency.

The preferred embodiment herein disclosed is not intended to unnecessarily limit the scope of the invention. Therefore, simple modifications or variations belonging to the equivalent of the scope of the claims and the instructions disclosed herein for a patent are all within the scope of the present invention.

What is claimed is:

1. A method of fabricating a diol containing a bis-cycloaliphate, the method comprising:

placing a catalyst comprising one or more active metal selected from a group consisting of nickel, platinum, palladium, ruthenium (Ru), and rhodium (Rh) and a catalyst carrier of an oxide of one or more of titanium, zirconium, or hafnium in a reactor;

placing a diol solution comprising a diol selected from a group consisting of bisphenol A (BPA) and ethoxylated bisphenol A (BPAEO) where the BPAEO has a structure as follows:

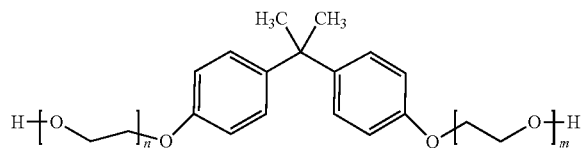

and m+n=2~4 and a solvent with hydrogen in the reactor; and processing a reaction at 60 bar or less and at 40~120° C. to obtain a product having a structure of

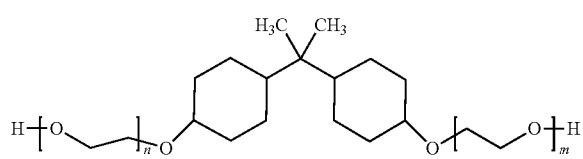

where m+n=2 to 4.

2. The method according to claim 1, wherein said solvent is selected from a group consisting of a monohydric alcohol and a combination of monohydric alcohols, said monohydric alcohol being selected from a group consisting of methanol, ethanol, propanol, isopropanol, isobutanol, cyclohexanol, and nonanol.

3. The method according to claim 1, wherein said active metal occupies 0.5~8 weight percent of said catalyst.

4. The method according to claim 1, wherein said reactor has a pressure of 1~50 bar.

5. The method according to claim 1, wherein said reaction has a temperature of 50~100 degrees Celsius.

6. The method according to claim 1, wherein said reactor is selected from a group consisting of a batchwise reactor, a stir-tank reactor, a trickle-bed reactor, a bubble-column reactor, and a multi-tube reactor.

\* \* \* \* \*